US 9,713,453 B2

(12) United States Patent
Brown et al.

(10) Patent No.: US 9,713,453 B2
(45) Date of Patent: Jul. 25, 2017

(54) METHOD AND APPARATUS FOR HIGH RELIABILITY WIRELESS COMMUNICATIONS

(71) Applicant: NeoCoil, LLC, Pewaukee, WI (US)

(72) Inventors: Brian Brown, Wauwatosa, WI (US);
Steven Wolff, New York, NY (US);
Andrew Shaw, Wauwatosa, WI (US);
Mark S. Geisler, Franklin, WI (US)

(73) Assignee: NeoCoil, LLC, Pewaukee, WI (US)

( * ) Notice: Subject to any disclaimer, the term of this patent is extended or adjusted under 35 U.S.C. 154(b) by 70 days.

(21) Appl. No.: 14/801,433

(22) Filed: Jul. 16, 2015

(65) Prior Publication Data

US 2016/0021219 A1    Jan. 21, 2016

Related U.S. Application Data

(60) Provisional application No. 62/025,171, filed on Jul. 16, 2014.

(51) Int. Cl.
| | |
|---|---|
| *A61B 6/03* | (2006.01) |
| *A61B 6/00* | (2006.01) |
| *A61B 5/055* | (2006.01) |
| *A61B 5/0402* | (2006.01) |
| *A61B 5/0205* | (2006.01) |

(Continued)

(52) U.S. Cl.
CPC ............ *A61B 6/541* (2013.01); *A61B 5/0022* (2013.01); *A61B 5/0205* (2013.01); *A61B 5/0402* (2013.01); *A61B 5/055* (2013.01); *A61B 5/7285* (2013.01); *A61B 6/03* (2013.01); *A61B 6/032* (2013.01); *A61B 6/503* (2013.01); *A61B 6/566* (2013.01); *G01R 33/3692* (2013.01); *G01R 33/5673* (2013.01); *G06F 19/3406* (2013.01); *H04L 1/201* (2013.01); *H04L 67/12* (2013.01); *H04L 67/125* (2013.01); *H04L 69/02* (2013.01);

(Continued)

(58) Field of Classification Search
CPC ....... H04L 67/12; H04L 67/125; H04L 69/02; H04L 69/14; H04W 4/005; H04W 4/008; H04W 72/048; H04W 84/18
See application file for complete search history.

(56) References Cited

U.S. PATENT DOCUMENTS

| | | | |
|---|---|---|---|
| 5,335,664 A * | 8/1994 | Nagashima | ......... A61B 5/0002 128/903 |
| 6,052,614 A | 4/2000 | Morris, Sr. et al. | |

(Continued)

OTHER PUBLICATIONS

Invivo Corporation; Invivo Expression MRI Monitor Brochure, 2009—(9) pages.

(Continued)

*Primary Examiner* — Mohamed Kamara
(74) *Attorney, Agent, or Firm* — Boyle Fredrickson, SC

(57) ABSTRACT

A physiologic transmitter manages multiple communications between physiologic data acquisition devices attached to the patient and a receiver attached to an MRI or CT scanner. The transmitter's processor is able to generate waveform data and trigger data based upon the acquired physiologic data and transmit the data to a physiologic receiver attached to the host scanner. The receiver then is able to deliver a trigger signal to the host scanner for imaging the patient during a selected time frame based upon cardiac and/or respiratory cycles of the patient.

20 Claims, 7 Drawing Sheets

(51) Int. Cl.
    *A61B 5/00*     (2006.01)
    *H04L 1/20*     (2006.01)
    *H04L 29/08*     (2006.01)
    *H04L 29/06*     (2006.01)
    *G06F 19/00*     (2011.01)
    *G01R 33/36*     (2006.01)
    *G01R 33/567*     (2006.01)
    *A61B 5/024*     (2006.01)
    *A61B 5/08*     (2006.01)

(52) U.S. Cl.
    CPC ............ H04L 69/14 (2013.01); *A61B 5/024* (2013.01); *A61B 5/0816* (2013.01)

(56) References Cited

U.S. PATENT DOCUMENTS

| | | | |
|---|---|---|---|
| 6,070,097 | A | 5/2000 | Kreger et al. |
| 6,611,705 | B2 | 8/2003 | Hopman et al. |
| 6,711,434 | B2 | 3/2004 | Kramer et al. |
| 6,749,566 | B2 | 6/2004 | Russ |
| 6,819,718 | B1 * | 11/2004 | Koehn ............... H04L 1/004 375/242 |
| 7,039,455 | B1 | 5/2006 | Brosovich et al. |
| 7,197,357 | B2 | 3/2007 | Istvan et al. |
| 7,272,428 | B2 | 9/2007 | Hopman et al. |
| 7,283,860 | B2 | 10/2007 | Frazier et al. |
| 7,403,808 | B2 | 7/2008 | Istvan et al. |
| 7,595,697 | B2 | 9/2009 | Tuccillo |
| 7,595,723 | B2 | 9/2009 | Heitzmann et al. |
| 7,689,270 | B2 | 3/2010 | Kwapil et al. |
| 7,738,943 | B2 | 6/2010 | Sha et al. |
| 7,751,785 | B2 | 7/2010 | Carvalho et al. |
| 7,860,557 | B2 | 12/2010 | Istvan et al. |
| 7,920,912 | B2 | 4/2011 | Harris et al. |
| 8,098,149 | B2 | 1/2012 | Fisher et al. |
| 8,121,667 | B2 | 2/2012 | Fisher et al. |
| 8,255,041 | B2 | 8/2012 | Istvan et al. |
| 8,294,588 | B2 | 10/2012 | Fisher et al. |
| 8,380,285 | B2 | 2/2013 | Frank et al. |
| 8,449,471 | B2 * | 5/2013 | Tran ................. A61B 5/0022 600/485 |
| 8,591,430 | B2 * | 11/2013 | Amurthur ........... A61B 5/0002 600/529 |
| 8,600,690 | B2 | 12/2013 | Ladebeck et al. |
| 8,626,266 | B1 | 1/2014 | Frank et al. |
| 2005/0276245 | A1 * | 12/2005 | Hidaka ................ H04L 1/0009 370/328 |
| 2006/0235281 | A1 | 10/2006 | Tuccillo |
| 2006/0241392 | A1 | 10/2006 | Feinstein et al. |
| 2009/0285322 | A1 * | 11/2009 | Imamura .............. H04B 7/0452 375/267 |
| 2011/0002427 | A1 * | 1/2011 | Hamamoto .......... H04B 7/0854 375/347 |
| 2011/0268037 | A1 * | 11/2011 | Fujimoto .............. H04B 7/043 370/328 |
| 2012/0114025 | A1 * | 5/2012 | Gauthier ............. H04B 7/0811 375/219 |
| 2013/0231574 | A1 | 9/2013 | Tran |
| 2014/0275970 | A1 * | 9/2014 | Brown ............... G01R 33/3692 600/413 |
| 2014/0369444 | A1 * | 12/2014 | Park ........................ H04L 27/06 375/302 |

OTHER PUBLICATIONS

Ivy Biomedical Systems, Inc.; Operation Manual Model 3150-B Cardiac Trigger Monitor; OM3150-B, Apr. 14, 2010, 2718-24-16 Rev. 01—(52) pages.

* cited by examiner

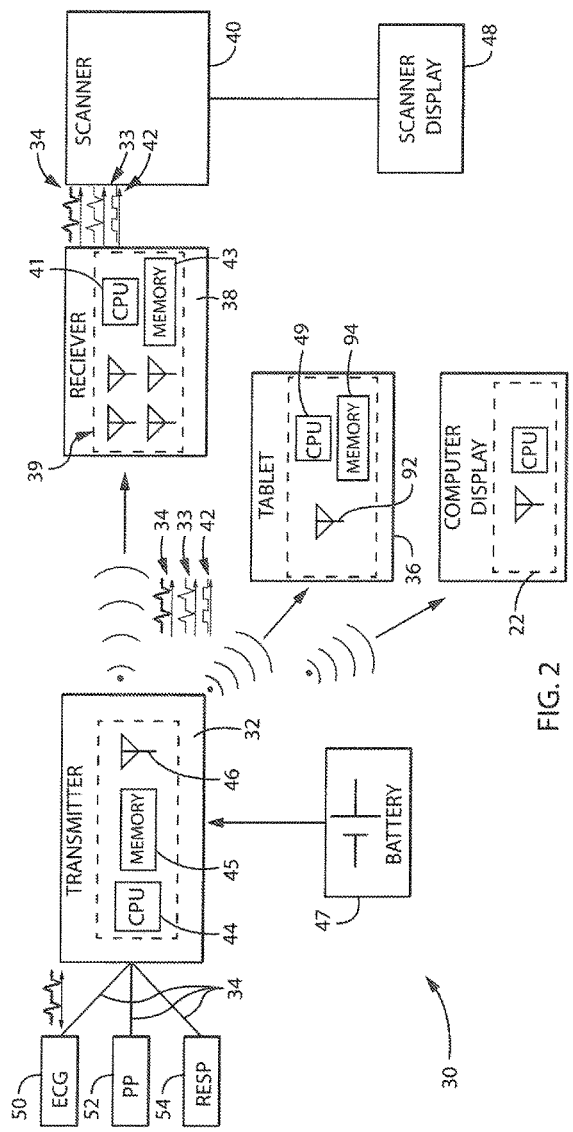

METHOD AND APPARATUS FOR HIGH RELIABILITY WIRELESS COMMUNICATIONS

CROSS-REFERENCE TO RELATED APPLICATIONS

This application claims priority to U.S. provisional application Ser. No. 62/025,171, filed Jul. 16, 2014, the entire contents of which is incorporated herein by reference.

BACKGROUND OF THE INVENTION

The subject matter disclosed herein relates to a wireless communication protocol and an exemplary application of the wireless communication protocol implemented with respect to a system for magnetic resonance imaging (MRI) and computed tomography (CT) compatible wireless physiological gated imaging. More specifically, a system for obtaining physiological data of a patient, generating trigger signals for the MRI or CT scanner, and wirelessly communicating the physiological data and/or trigger signals in the MRI or CT environment is disclosed.

As is known to those skilled in the art, a magnetic resonance imaging (MRI) system alternately generates a strong magnetic field and then detects the faint nuclear magnetic resonance (NMR) signals given off by nuclei in the presence of the magnetic field. The NMR signals are received by antennas, also known as coils, and transmitted to the MRI scanner for reconstruction into an MRI image. In order to provide a clear image, it is desirable to minimize interference associated not only with external artifacts, such as electromagnetic interference, but also with motion artifacts, such as voluntary or physiologic motion.

As is also known to those skilled in the art, a computed tomography (CT) system takes a series of x-ray views of the desired object and reconstructs them to create cross-sectional images of the object. Many times, the tomographic slices may be combined to create 3-D images. A CT system relies upon x-ray particles being sent through the body and then detecting the amount of absorption or scattering of those particles to construct a representative image of the object based upon the density or other physical properties of the object or structure. Similar to an MRI scanner, a number of different artifacts may produce unwanted interference during a CT scan, such as motion artifact related to voluntary or physiologic motion.

Specifically, with respect to motion artifacts, MRI and CT imaging is complicated by the periodic motion of a patient, such as respiratory or cardiac motion. Cardiac motion includes, for example, motion of the heart and blood flow through blood vessels. Respiratory motion includes, for example, the expansion and contraction of the lungs and the resulting motion of the surrounding anatomy. Breath-holding is one technique utilized to minimize motion artifacts due to respiratory motion. However, due to the length of time required for some scans, breath-holding is not always practical. In addition, no such comparable technique may be employed to minimize cardiac induced motion artifacts.

However, much of the respiratory and cardiac induced motion is repeated over a certain cycle. Cardiac motion may be defined, for example, based on one cycle of an electrocardiogram (ECG). Respiratory may be defined on the basis of an inhalation/exhalation cycle. In order to reduce motion artifacts, certain points within each of the cycles may be identified. A peak value in the ECG or a maximum inhalation point may be identified. By obtaining successive images at the same point in the cycle, motion artifacts for the anatomy being imaged are reduced.

In order to trigger the MRI scanner or the CT scanner to obtain an image, however, a cycle must be measured and a trigger signal provided to the scanner to initiate image acquisition. The ability to reduce motion artifacts is impacted by the amount of time required between detecting the desired point in a cycle and initiating the image acquisition. The ability to reduce motion artifacts is similarly impacted by the repeatability of the amount of time, such that the anatomy being imaged is in the same relative position between images.

During imaging a number of physiological parameters of the patient may require monitoring. In order to reduce the number of cables and because cables may introduce artifacts as well, it is desirable to provide wireless sensors to monitor the physiological parameters of the patient. However, wireless communication may introduce transmission delays and/or repeatability issues between detecting the physiological parameter and transmitting the data.

Thus, it would be desirable to provide an improved transmission protocol for high reliability of transmission between wireless devices and, more particularly, for high reliability of transmission between wireless devices used for medical imaging.

BRIEF DESCRIPTION OF THE INVENTION

The subject matter disclosed herein describes a wireless transmission protocol developed for use with medical imaging scanners which provides high reliability of transmission between wireless devices with low latency and low jitter.

According to an exemplary embodiment of the invention, the wireless transmission protocol is implemented on an MRI and CT compatible physiological data acquisition system. The physiological data acquisition system includes an acquisition module configured to receive signals from physiologic sensors attached to the patient and a transmitter configured to wirelessly communicate with a receiver module. The acquisition module includes a processor operable to generate waveform data and trigger data based upon the acquired physiologic data and transmit the data to the receiver module. The receiver module is configurable to be attached to the either an MRI or a CT scanner. The receiver module then is able to deliver a trigger signal to the host scanner for imaging the patient during a selected time frame based upon the patient's cardiac cycle, peripheral pulse, respiratory cycle, or any combination thereof.

The physiological data acquisition system is configurable to transmit and/or receive data between physiological sensors, a physiologic transmitter, a physiologic receiver, a portable tablet or another computer, and a MRI scanner or CT scanner.

It is an objective of the present invention to provide a wireless physiological monitoring system that sends physiologic waveform and trigger data to diagnostic imaging scanners.

It is also an objective of the present invention to use a single physiologic transmitter for both MRI and CT triggering applications. Since many clinical sites run multiple scanners, a single transmitter can be used in conjunction with multiple physiologic receivers.

It is a further objective of the present invention to provide a wireless communication system which allows for low latency, low jitter, and high reliability in the transmission of a trigger signal.

According to one embodiment of the invention a wireless communication system, including a transmitter and receiver is disclosed. The transmitter includes a control circuit, a transmit circuit, and an antenna. The control circuit is operable to prepare a data packet for transmission, and the transmit circuit is in communication with the control circuit and operable to convert each data packet to a radio frequency (RF) signal for transmission. The antenna is in communication with the transmit circuit and operable to transmit the RF signal. The receiver includes at least one antenna operable to receive the RF signal, at least one receive circuit, and a control circuit. Each receive circuit is in communication with the at least one antenna and operable to convert the RF signal to a data packet. The control circuit is in communication with each receive circuit and operable to extract data from the data packet. The control circuit in the transmitter prepares the data packet for transmission at a periodic interval. The transmit circuit converts the data packet to a plurality of RF signals, where each RF signal has a different frequency, and transmits each RF signal within the periodic interval. The receiver receives the RF signals at each of the frequencies, converts each RF signal back to the data packet, and verifies that the data packet was transmitted successfully.

According to another aspect of the invention, the receiver includes an antenna and a receive circuit tuned to each of the frequencies at which the RF signals are transmitted, and the antenna and the receive circuit are operable together to receive the RF signal at the corresponding frequency. Optionally, the receiver includes one antenna and multiple receive circuits, where each receive circuit is tuned for one of the frequencies at which the transmitter transmits RF signals. The wireless communication system may also include a splitter in communication with the antenna and each receive circuit, where the splitter identifies the frequency of each RF signal received by the antenna and routes the RF signal to the corresponding receive circuit tuned for the frequency of the RF signal.

According to still another aspect of the invention, the receiver verifies that the data packet was transmitted successfully by comparing the data packets received at each of the frequencies. When a majority of the data packets are the same, the receiver uses one of the majority of identical data packets. Optionally, the transmitter includes a checksum in the data packet, and the receiver verifies that the data packet was transmitted successfully by determining that the checksum received corresponds to the data present in the data packet for at least one of the frequencies at which the data packet was transmitted.

According to yet another aspect of the invention, the transmitter may also include memory operable to store multiple values of data to be included in the data packet on a first-in-first-out (FIFO) basis, and the control circuit of the transmitter includes the plurality of values in the data packet.

According to still another aspect of the invention, the receiver includes a plurality of antennas. Each antenna is spatially displaced from the other antennas and is in communication with one of the receive circuits.

According to another embodiment of the invention, a method of wireless communication is disclosed. A data signal is received at a control circuit in a transmitter, and the control circuit generates a data packet, which includes at least one value of the data signal. The data packet is converted to a plurality of RF signals, where each RF signal has a different frequency. Each of the RF signals is transmitted within a periodic interval and received at a receiver in communication with the transmitter. The data packet is extracted from each of the RF signals in a control circuit in the receiver, and the control circuit evaluates the data packets to verify that the data packet was transmitted successfully.

According to another aspect of the invention, evaluating the data packets to verify that the data packet was transmitted successfully may include comparing the data packets extracted from each of the RF signals to each other and determining the data packet was transmitted successfully when a majority of the data packets are identical. Optionally, the control circuit of the transmitter may generate a checksum for the data packet and transmit the checksum along with the data packet. Evaluating the data packets to verify that the data packet was transmitted successfully may then include determining a checksum for each data packet in the control circuit of the receiver and determining the data packet was transmitted successfully when the checksum determined on the receiver matches the checksum transmitted from the transmitter.

According to still another aspect of the invention, multiple values of the data signal are stored in a memory device in the transmitter on a first-in-first-out basis, and each of the values is included in the data packet when the data packet is generated. Each of the values is extracted from the data packet and stored in a memory device on the receiver in the receiver. The number of data packets is the same as the number of values. Evaluating the data packets to verify that the data packet was transmitted successfully may include comparing the value of the data signal in each data packet to the corresponding value in each of the other data packets in which it is transmitted. It is determined that the value of the data signal was transmitted successfully when the corresponding values of the data signal from a majority of the data packets in which the value is transmitted are identical. Optionally, the control circuit of the transmitter may generate a checksum for the data packet and transmits the checksum along with the data packet. Evaluating the data packets to verify that the data packet was transmitted successfully may include determining a checksum for each data packet in the control circuit of the receiver. It is then determined that each value of the data signal in one of the data packets was transmitted successfully when the checksum determined on the receiver matches the checksum transmitted from the transmitter According to yet another aspect of the invention, the receiver includes a plurality of antennas, each antenna spatially displaced from the other antenna. Receiving each of the RF signals at a receiver in communication with the transmitter includes receiving each of the RF signals at each antenna. Each of the RF signals from each antenna is transmitted to a receive circuit in communication with the antenna, and the data packet is extracted from each of the RF signals received at each antenna. Evaluating the data packets to verify that the data packet was transmitted successfully may include comparing each of the data packets transmitted at one of the frequencies and received at each of the antennas to each other. It may be determined that the data packet at one of the frequencies was transmitted successfully when a majority of the data packets received at each antenna are identical. The successfully transmitted data packet at each frequency are then compared to the successfully transmitted data packet at each of the other frequencies. It may be determined that the data packet was successfully transmitted when a majority of the successfully transmitted data packets at each frequency are identical.

According to still another aspect of the invention, the data signal received is from a sensor generating a signal corresponding to a physiological parameter of a patient to which the sensor is connected, and the transmitter and receiver are utilized with a medical imaging scanner. The data signal may be processed in the control circuit of the transmitter to generate either a filtered data signal or a trigger signal, and the data packet may include the trigger signal. The trigger signal is extracted from the data packet with the control circuit of the receiver and transmitted to the medical imaging scanner to initiate acquisition of an image of the patient.

These and other objects, advantages, and features of the invention will become apparent to those skilled in the art from the detailed description and the accompanying drawings. It should be understood, however, that the detailed description and accompanying drawings, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWING(S)

Various exemplary embodiments of the subject matter disclosed herein are illustrated in the accompanying drawings in which like reference numerals represent like parts throughout, and in which:

FIG. 2 is a block diagram representation of one embodiment of a trigger monitor system according to the present invention;

FIG. 3 is a block diagram representation of the transmitter of FIG. 2;

Figure 1:
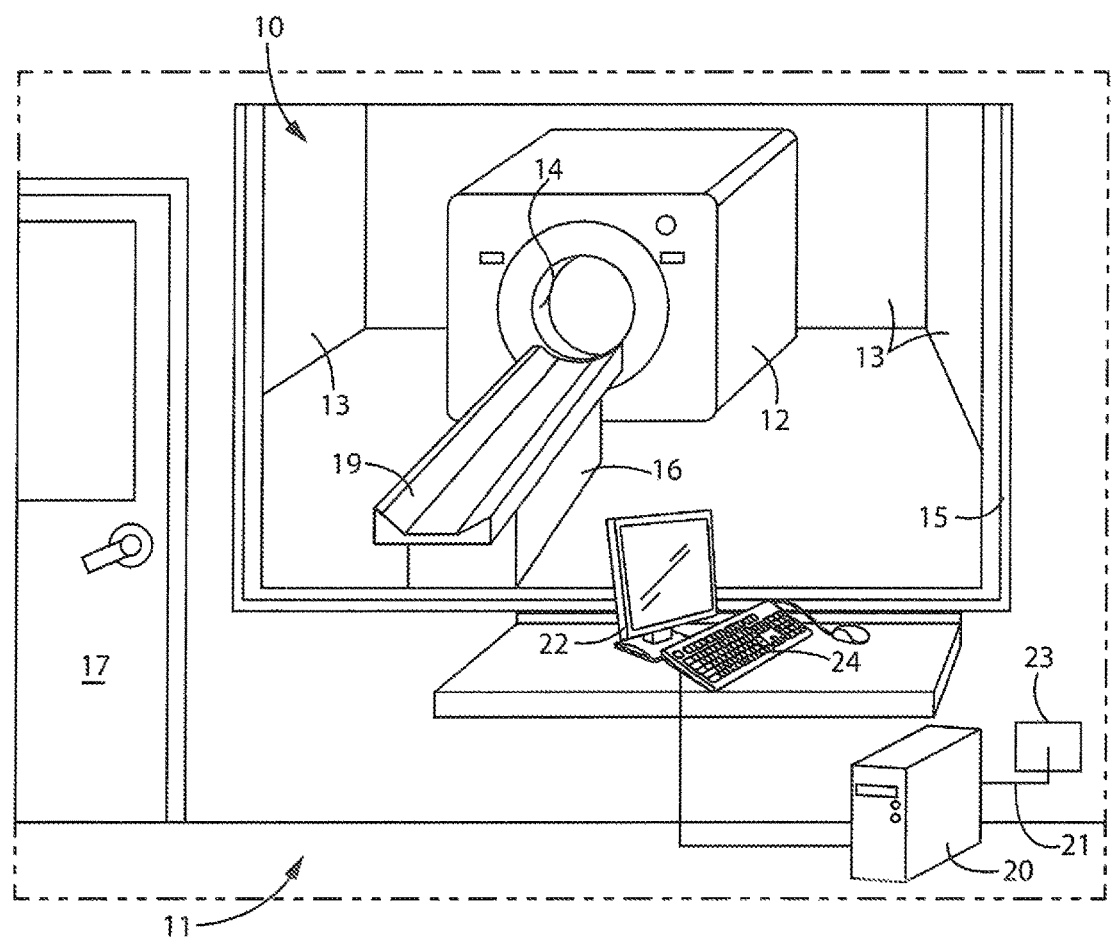
FIG. 1 is a exemplary embodiment of an existing MRI scan room.

In describing the preferred embodiments of the invention which are illustrated in the drawings, specific terminology will be resorted to for the sake of clarity. However, it is not intended that the invention be limited to the specific terms so selected and it is understood that each specific term includes all technical equivalents which operate in a similar manner to accomplish a similar purpose. For example, the word "connected," "attached," or terms similar thereto are often used. They are not limited to direct connection but include connection through other elements and/or wireless connection where such connection is recognized as being equivalent by those skilled in the art.

DETAILED DESCRIPTION OF THE PREFERRED EMBODIMENTS

The various features and advantageous details of the subject matter disclosed herein are explained more fully with reference to the non-limiting embodiments described in detail in the following description.

Trigger Monitor System

According to one embodiment of the present invention, a trigger monitor system, which interfaces with MRI and CT scanners, for use on patients requiring image acquisition synchronization is disclosed. The trigger monitor system may be implemented in a MRI environment as shown in FIG. 1. Alternatively, the present invention may be implemented in a CT environment as understood in the art. The CT environment is similar to the MRI environment with a CT scanner replacing the MRI scanner. Similar problems of interference and motion artifact exist in both environments. The present invention allows the same trigger monitoring system to be used in either environment, regardless of the type of host scanner being used.

Referring to FIG. 1, an exemplary shielded room 10 containing an MRI scanner 12 is illustrated. The scan room 10 includes walls 13, or panels, which typically incorporate RF shielding within the wall 13. A window 15 permits an operator to observe activity within the scan room 10 from an adjacent control room 11, typically connected via a door 17. The door 17 may similarly incorporate RF shielding within the solid portion of the door. The window 15 between the scan room 10 and the control room 11 and, if present, a window in the door 17 are covered in a conductive material such as a fine wire mesh or a thin metallic foil made, for example, from copper or gold to provide RF shielding on the window. The shielding is configured to prevent external RF signals that are in a spectrum that may interfere with the MRI scanner 12 from entering the scan room 10 and causing said interference.

A controller 20 for the MRI scanner 12 is typically located in the adjacent control room 11. An operator interface including, for example, a monitor 22 or other display unit and an input device such as a keyboard 24 are connected to the controller 20. The controller 20 may be connected to the MRI scanner 12 by cabling extending, for example, under the floor of the scan room 10 or in a shielded conduit to the MRI scanner 12. A penetration panel 23 in the wall may also provide connections to cables 21 running from the controller 20 into the scan room 10. The penetration panel 23 may include connectors for cabling to other medical equipment present in the scan room 10. Corresponding connectors on the other side of the penetration panel 23 within the scan room 10 permit appropriately shielded cables to be connected and run to the scanner 12 or to other medical equipment. A table 16 supports the patient being scanned and typically includes a sliding platform 19 allowing the patient to be moved into and out of the bore 14 of the MRI scanner 12.

Referring next to FIG. 2, one embodiment of a trigger monitor system 30 is shown as a block diagram. The trigger monitor system 30 is compatible with MRI and CT scanners and can communicate wirelessly with a MRI or CT scanner to deliver a trigger signal 42. The trigger monitor system 30 contemplates a physiological acquisition device or physiologic transmitter 32, which receives physiological signals 34 from a number of sensors placed on a patient's body. It is contemplated that the physiologic transmitter 32 may convert the raw physiologic signals directly to a RF signal for transmission or first perform processing of the physiologic signal 34 to generate a filtered waveform 33 representing the measured signal. It is further contemplated that the physiologic transmitter 32 may perform further processing on either the raw data 34 or the filtered waveform 33 to generate a trigger signal 42 for the host scanner 40. The physiologic transmitter 32 may then wirelessly transmit the raw physiologic signal 34, the filtered waveform 33, the trigger signal 42, or a combination thereof to an external computer display, e.g., a computer monitor 22 located in the scan room 10 or in the control room 11, or a portable device such as a tablet 36, so that an operator may view the waveform data during operation.

The physiologic receiver 38 receives the data from the physiologic transmitter 32 and sends the data to the host scanner 40. A display 48 connected to the scanner 40 may provide a visual indication of the raw physiologic signal 34, the filtered waveform 33, the trigger signal 42, or a combination thereof. It is contemplated that the receiver 38 may transmit just raw physiologic signals 34 to the scanner 40 and the scanner 40 may perform further processing on the data. Optionally, the scanner 40 may be configured to receive the filtered waveform 33 and/or the trigger signal 42 and to perform further processing or to capture image data responsive to any of the data transmitted from the receiver 38. Thus, the scanner 40 may either process the raw physiologic signal 34 or the filtered waveform 33 data to generate a gating signal or utilize the gating signal 42 from the transmitter 32 for image triggering. The host scanner 40, which may be either an MRI or CT scanner, may also display the trigger signal 42 on the scanner display 48 to provide a visual indication to the operator of when imaging occurs. If the physiologic transmitter 32 generates and sends a trigger signal to the physiologic receiver 38, the physiologic receiver 38 may pass the trigger signal directly to the host scanner 40.

According to another embodiment of the invention, the physiologic receiver 38 may be configured to perform processing on the raw data 34 or the filtered waveform 33 received from the physiologic transmitter 32 to generate a trigger signal 42. The physiologic receiver 38 may perform further processing to format the trigger signal 42 and/or encapsulate the trigger signal in a message packet suitable for transmission to the host scanner 40 to which the physiologic receiver 38 is connected. The trigger monitor system 30 described herein allows the host scanner 40 to synchronize image acquisition responsive to the trigger signal, which may be required to eliminate motion artifacts and/or to obtain images at specific intervals within the cardiac or respiratory cycles.

According to the illustrated embodiment of the invention, the physiologic transmitter 32 of the trigger monitoring system 30 performs the function of interpreting physiologic signals 34 that it receives and turning it into waveform data. The physiologic transmitter 32 acquires physiological signals 34 from the patient as commonly known in the art. The transmitter processor or CPU 44 may receive raw data for certain body vital sign parameters, e.g., electrocardiogram (ECG) 50, peripheral pulse (PP) 52, and respiratory rate (RESP) 54. For each parameter, physiologic sensors or physiological acquisition devices unique to each parameter are used. Each of the physiologic sensors or devices will be described in greater detail below. The physiologic sensors, e.g., electrodes, are attached to the patient's body at various detection locations. Connectable leads or electrical connectors couple the physiologic sensors to the physiologic transmitter 32 via ports located on the physiological transmitter module.

According to one aspect of the present invention, ECG data 50 is collected from the patient. In collecting ECG data 50 from a patient, a number of surface electrodes are placed on the patient's chest at particular locations. For example, for MRI applications, a first electrode is placed at a first intercostal space, just left of the sternum. A second electrode is positioned at the level of the xyphoid, just left of the sternum. A third electrode is positioned on the patient's left side, horizontally aligned with the second electrode, and a fourth electrode is placed close to the left armpit. For CT applications, the electrodes may be configured in a box configuration around the torso. Each electrode is proximate to a limb of the patient where, for example, a first electrode is positioned at the right shoulder proximate the right arm, a second electrode is positioned at the left shoulder proximate the left arm, a third electrode is positioned at the left hip proximate the left leg, and a fourth electrode is positioned at the right hip proximate the right leg. The electrodes are connected to leads, often facilitated by conducting alligator clips, which deliver electrical activity information to the physiologic transmitter 32.

Due to differences in imaging physics, the electrode placement used for ECG may differ between MRI and CT, as described above. Different types of electrodes and/or leads may also be required for different types of scanners. The physiologic transmitter 32 according to the illustrated embodiment is able to detect the difference between the electrodes/leads attached to it and differentiates between MRI and CT. Depending on the particular scanner 40 that is being used, MRI or CT, the physiologic transmitter 32 can select the correct format and type of data to interpret and transmit. The physiologic transmitter 32 can also instruct the operator to place the ECG leads on the appropriate thoracic locations specific to MRI or CT, as visualized on the physiologic transmitter interface 62 and further described below.

According to another aspect of the present invention, peripheral pulse data 52 is collected from the patient. To collect peripheral pulse data 52, photoplethysmography may be used whereby pulses in the blood radiating to the periphery of the patient after each heartbeat can be detected. Pulses may be detected by using a photoplethsmograph connected to the patient's finger. The photoplethsmographs passes light at a desired wavelength, such as infrared (IR) or in the red spectrum, through the patient's finger to a photodetector. The light absorbance changes during a cardiac cycle and, therefore, the amount of light reflected and/or absorbed is measured, allowing determination of the absorbances due to the pulsing arterial blood. Photoplethysmography can also be connected on the patient's forehead in a similar matter but measuring the reflection of the light. Peripheral pulses 52 can alternatively be acquired by placing sensors at a patient's neck, wrist, foot, etc.

According to yet another aspect of the present invention, respiratory rate data 54 is collected from the patient. When collecting a patient's respiratory rhythm 54, a respiratory bellow or sensor pillow may be placed on a patient's chest or stomach region for recording their respiratory cycle. The sensor pillow is secured to the patient such that expansion and contraction of the chest or abdominal region during a respiratory cycle causes compression and decompression of the sensor pillow. The sensor pillow generates a signal corresponding to the compression and decompression and transmits the signal to the physiologic transmitter 32. The breathing cycle may be monitored to minimize breathing interference or allow the operator to assess the patient's level of consciousness during a scan. Optionally, the respiratory cycle may be monitored via the ECG electrodes by monitoring impedance changes across the chest between ECG electrodes. During the respiratory cycle, the rising and falling motion of the chest results in a varying impedance between electrodes.

In MRI and CT applications, the physiologic transmitter 32 can support three physiological parameters simultaneously, two physiological parameters simultaneously, or any one physiological parameter individually. It is understood that MRI and CT may require different sets of parameters; however, some or all of the parameters may be used for each scan application. For example, MRI scanning may utilize all three parameters, while CT scanning typically only utilizes the ECG data. It is understood that more than three physiological parameters may also be utilized while still remaining within the scope of the invention described herein. Each physiologic sensor may be connected and transmit a physiologic signal 34 to the physiologic transmitter 32 via a wired or wireless connection.

Referring now to FIG. 3, the physiologic transmitter 32 includes a processor or CPU 44 that is able to receive and interpret the physiologic parameter signals 34 received from the sensors, as described above. A series of instructions, or a program, is stored on a memory device 45 on the physiologic transmitter 32. The memory device 45 may be a single device or multiple devices and may include persistent memory, non-persistent memory, or a combination thereof. Optionally, a portion or all of the memory device 45 may be integrated on a single device with the processor 44. The processor 44 will execute the stored application to take the raw sampled physiological signals 34 and use a filtering process 35 to eliminate interference found in the signals 34 to create a waveform image. For example, filtering is used to remove noise existing in the waveform image. The filter used may be selected according to each specific waveform, i.e., ECG, PP, or RESP waveforms. The processor 44 will create a filtered waveform, e.g., a cardiac waveform, a peripheral pulse waveform, or a respiratory waveform, which is transmitted to a receiver or be further processed for gating analysis.

The processor 44 will further execute a stored application to perform trigger or gating analysis 37 on the filtered waveform. This analysis produces a gating signal 42 used to coordinate timing between data acquisition from the MRI or CT scanner 40 and receiving and recording the data for generation of an MRI or CT image. According to one embodiment of the invention, the gating signal is generated by the processor 44 as a function of the physiological data received to coordinate imaging, for example, with the heart beat or respiration of the patient. Gating may be performed using R-wave detection followed by gating methods, such as amplitude or vector gating. In the process of performing gating analysis 37 the processor 44 may compute peak levels for each parameter. The processor 44 will also create heart rate data to be provided to the operator.

The processor 44 sends the waveform, peak information, and heart rate data to the radio 46 of the physiologic transmitter 32 for wireless transmission. The physiologic transmitter radio 46 then transmits this information wirelessly to a physiologic receiver 38 and/or portable tablet 36 or external computer monitor 22, which may be done via Bluetooth, WiFi, or another form of wireless protocol, which will be further described herein. The processor 44 performs the function of controlling transmission of the radio 46. Transmission between the physiologic transmitter 32 and receivers 38 are typically one-way but it is contemplated that data may be exchanged in both directions.

Figure 4:
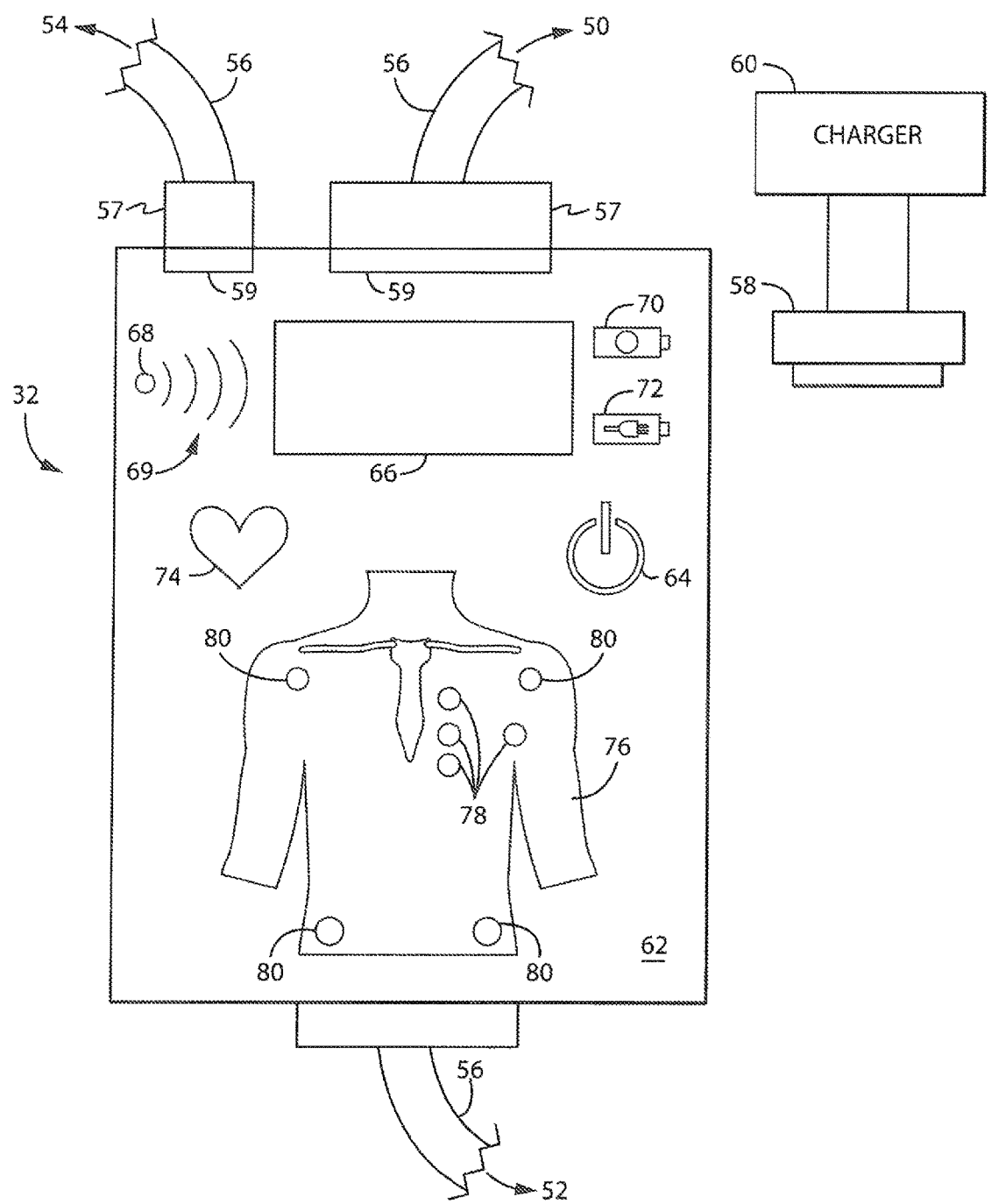
FIG. 4 is a schematic representation of the transmitter interface of FIG. 2.

Referring next to FIGS. 2 and 4, the physiologic sensors may be connected to the physiologic transmitter 32 using leads 56 and electrical connectors 57. Optionally, the physiologic sensors may transmit data wirelessly to the physiologic transmitter 32. The physiologic transmitter 32 has separate ports 59 for receiving the electrical connectors 57 for, e.g., ECG, PP, and RESP signals 34. The physiologic transmitter 32 may include an integrated rechargeable battery 47 for supporting at least a day's use before recharging. The physiologic transmitter 32 is recharged by connecting a charger 60 to the transmitter 32. The charger 60 may itself include a battery from which it supplies power to the transmitter 32 or the charger 60 may be configured to connect to a utility power source. The charger 60 is configured to convert the voltage from a first level, such as a 120 VAC utility supply, to a second level, such as 5 or 12 VDC, suitable for charging the battery 47 in the physiologic transmitter 32. To enhance patient safety a connector 58 from the charger 60 may be configured to be inserted into the same port 59 as the ECG connector 57 and power is delivered to the rechargeable battery 47 via this port 59. Thus, the rechargeable battery 47 may only be recharged by the recharger 60 by removing the ECG connector 56 from the physiologic transmitter 32 and inserting the connector 58 for the recharger 60 in its place, allowing only one to be inserted one at a time. By doing so, the system ensures that the patient is never connected to the physiologic transmitter 32 at the same time that the physiologic transmitter 32 is attached to an electrical power source.

The physiologic transmitter interface 62 may include a number of visual displays for relaying information to the operator and enhancing operation. In one embodiment of the present invention, the physiologic transmitter 32 has an interface 62 which may include an on/off button 64 for powering the module "on" when desired and powering the module "off" when not in use and in order to conserve the battery life. A digital display 66, such as a LCD display, may display the heart rate of the patient, which may be determined by, e.g., the ECG or peripheral pulse data. Optionally, device status and/or information for the technologist may be displayed. The physiologic transmitter 32 may also include a selection button or buttons, which may be pressed to select each waveform or a combination of waveforms to be sent to the physiologic receiver 38 or to be used to determine the trigger signal 42. The selected waveform may be identified, for example, on the digital display 66, by one or more LEDs located on the physiologic transmitter 32, or by any other suitable visual indicator.

The physiologic transmitter interface 62 may include a number of indicator lights, which may be in a first lit state or a second unlit state to relay information or provide alerts to the operator. A first indicator light may be a wireless indicator light 68 that becomes lit to indicate that wireless communication is functioning. The wireless indicator light 68 may include multiple "bars" 69, where a varying number of the bars 69 are illuminated to indicate the strength of a wireless connection between the transmitter 32 and another device. Optionally, the wireless indicator light may also display a different color light to indicate varying strength of the wireless connection. It is contemplated that the wireless communication may be, e.g., WiFi, Bluetooth, a proprietary protocol, as will be further discussed herein, or a combination thereof. The physiologic transmitter 32 may, for example, be configured to communicate with a tablet computer 36 via a WiFi connection and with the physiologic receiver 38 via the proprietary protocol. Another indicator light may be a battery indicator light 70 indicating that the device is fully charged. The battery indicator light 70 may also display a different color light to indicate that battery power is low or a blinking feature to indicate low battery life remaining. Another indicator light may be a charge notification light 72, which may become lit to indicate that the battery is currently being charged. The charge notification symbol 72 may be an icon in the shape of a plug or lighting strike. Another indicator light may be a heart rate indicator 74. If the indicator light 74 is lit, it is an indication that all leads 56 of a ECG are receiving data and a heart rate can be properly displayed from the ECG data. If the indicator light 74 is off, it is an indication that a lead(s) 56 has fallen off and/or ECG data is not being properly gathered. The heart rate indicator 74 may be in the form of a heart shaped icon. The transmitter 32 may also generate and transmit a message containing data corresponding to its operating status, such as the battery life and lead connection/operation status. The message may be transmitted either via a standard wireless protocol or via the proprietary protocol to another device in communication with the transmitter 32.

The physiologic transmitter interface 62 may also include a representation of a patient's torso 76 with a number of position indicator lights 78, 80 representative of the positioning of the surface electrodes on the patient's torso. Further, a first set of position indicator lights 78 may represent the positioning of the surface electrodes on the patient's torso during an MRI scan and a second set of position indicator lights 80 may represent the positioning of the surface electrodes on the patient's torso during a CT scan. Each set of leads 56 may require different characteristics. For example, the positioning of the leads 56 may require different lead lengths or the operating environment of an MRI scanner may have different shielding requirements for the leads 56 than for a CT scanner. The leads 56, therefore, may include an identifier incorporated, for example, in the electrical connector 57 for the lead 56. The identifier may be, for example, a set of jumpers corresponding to a bit pattern, an identification resistor having a different value for different lead sets, or any other suitable method of identifying the lead set. The physiologic transmitter 32 may be configured to detect the identifier and determine whether the set of leads is to be used for an MRI scan or a CT scan. Optionally, a single set of leads suitable for both an MRI scan and a CT scan may be provided. The physiologic transmitter 32 may receive a signal transmitted from the physiologic receiver 38 indicating whether the leads are to be configured for an MRI scan or a CT scan, where the physiologic receiver 38 has detected the type of scanner from a cable 100 connected between the physiologic receiver 38 and the host scanner 40 as discussed in more detail below. If, for example, the leads are to be used for an MRI scan, the interface will light the first set of position indicator lights 78 corresponding with the correct positioning for MRI. If the lead set is to be used for a CT scan, the interface will light the second set of position indicator lights 80 corresponding with the proper positioning for CT.

It is further contemplated that a different set of leads may be used for pediatric and adult imaging, and separate identifiers may be used for the pediatric and adult leads. In addition to detecting the type of scanner to which it will be connected, the physiologic transmitter 32 may detect if pediatric or adult imaging is to be performed. The physiologic transmitter 32 may include different filtering or gating algorithms based on whether pediatric or adult imaging is to be performed and execute the corresponding algorithm according to the detected identifier.

The position indicators 78, 80 may further indicate whether the leads are properly connected to the patient. The position indicators 78, 80 may be configured to operate in a first state and a second state. For example, the first state may be displaying a first color while the second state may be displaying a second color. Optionally, the first state may be a blinking light while the second state may be a solid light. In both the first and the second states, the position indicators 78, 80 function to provide an indication of the proper positioning of the leads on the patient's torso. In the first state, the position indicators 78, 80 will indicate that each of the leads are properly connected to the electrodes and in communication with the physiologic transmitter 32. In the second state, the position indicators 78, 80 will identify each lead not properly connected to the electrode or not in communication with the physiologic transmitter 32, for example, if a conductor within the lead fails. According to the illustrated embodiment, the position indictors 78, 80 will light in a first color, such as green, to show that each lead of the ECG cable is properly attached and that transmitter 32 is receiving electrical signals from each of the electrodes of the ECG. The position indicators 78, 80 will light in a second color, such as red, if the corresponding electrode has become detached or the lead has failed, alerting the operator of a problem with the lead set. It is further contemplated that the transmitter 32 may generate a data message to be transmitted to the receiver 38 providing the status of the leads connected to the patient.

Figure 5:
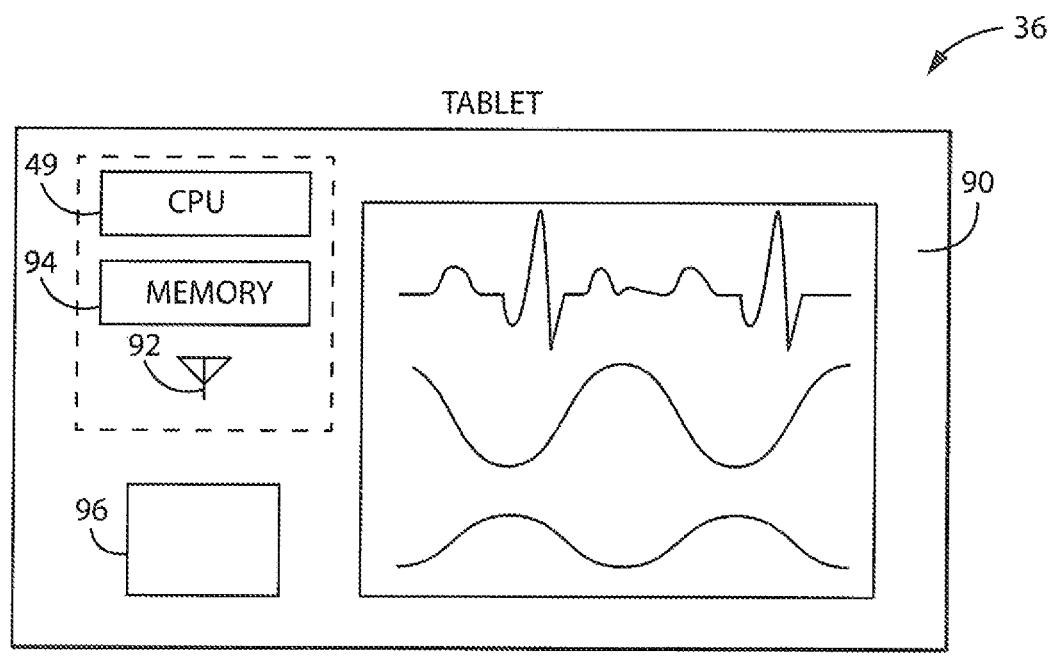
FIG. 5 is a schematic representation of the tablet interface of FIG. 2.

Referring next to FIGS. 2 and 5, the trigger monitoring system 30 may include a tablet computer 36 incorporating a wireless communication module. As described above, data may be transmitted wirelessly to a receiver of a portable device, such as tablet 36 or another external computer monitor 22. Bluetooth or WiFi may be used for communication to a tablet computer 36 because of the compatibility with existing protocols on the tablet computer 36, but any form of wireless transmission may be used. The transmitter 32 may utilize a separate antenna for transmitting to the tablet computer 36.

The processor 49 of the tablet computer 36 executes a stored application to receive and/or transmit data via the wireless communication module and provide a visual representation of the data on a display 90 of the tablet computer 36. According to one embodiment of the invention, the wireless communication module is configured to communicate an appropriate communication standard, such as Bluetooth. Optionally, the wireless communication module may utilize any suitable communication protocol. Data is received by an antenna 92 connected to and typically integrated with the wireless communication module.

According to application requirements, the tablet 36 may store the data on a memory device 94 and/or provide a visual representation of the data on a display 90. The memory device 94 may be volatile or non-volatile. Optionally, the tablet 36 may be removed from the scan room 10 and taken to a remote location where the stored data may be transmitted to another device, such as another computer, a monitor or other display device or a printer.

The data displayed on the tablet 36 or another computer may, for example, correspond to the data measured by the physiologic transmitter 32. The physiologic waveforms, peak information, raw physiologic data, gating trigger, or a combination thereof may be displayed on the tablet display 90 in order for the operator to make a qualitative assessment of the patient condition while undergoing the exam. When a tablet 36 or computer receives data from the physiologic transmitter 32, the display 90 may show one or more waveforms of the physiologic data, the trigger data, heart rate, pulse rate, or respiratory rate simultaneously on the display 90 and in substantially real time. The tablet 36 is able to display multiple parameters, such as ECG, respiratory waveforms and peripheral pulse waveforms. The display 90 may also show the trigger rate and trigger pulse data 96. The display 90 may also allow the waveforms to change colors to indicate that a lead has become detached, thus alerting the operator.

Referring again to FIG. 2, the trigger monitoring system 30 includes a physiologic receiver 38 also incorporating a wireless communication module. A series of instructions, or a program, is stored on a memory device 43 on the physiologic receiver 38. The memory device 43 may be a single device or multiple devices and may include persistent memory, non-persistent memory, or a combination thereof. Optionally, a portion or all of the memory device 43 may be integrated on a single device with the processor 44. The physiologic receiver 38 executes the stored application to receive and/or transmit data via the wireless communication module and send a trigger signal 42 to an attached host scanner 40. According to one embodiment of the invention, the wireless communication module of the physiologic receiver 38 is configured to communicate with the physiologic transmitter 32 via a proprietary protocol discussed in more detail below. Optionally, the wireless communication module may utilize any suitable wireless communication standard. Data is received by an antenna 39, or one of multiple antennas, connected to and typically integrated with the wireless communication module.

The physiologic receiver 38 is configured to receive the data transmitted by the physiologic transmitter 32. According to application requirements, the physiologic receiver 38 may store the data on the memory device 43. The memory device may be volatile or non-volatile. The manner in which the physiologic receiver 38 uses the information provided from the physiologic transmitter is governed by the physiologic receiver 38 as well as by the preference of the technologist performing the examination.

Figure 6:
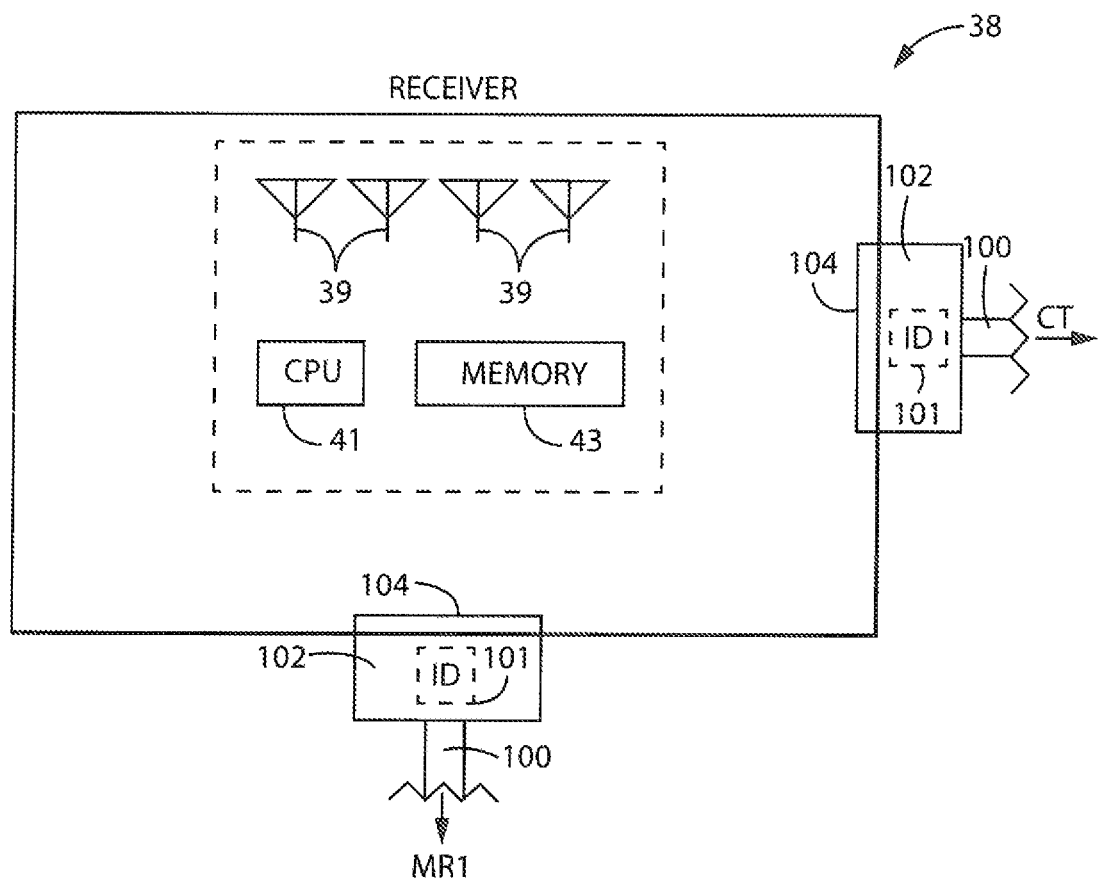
FIG. 6 is a schematic representation of the receiver interface of FIG. 2.

Referring next to FIGS. 2 and 6, a processor or CPU 41 of the physiologic receiver 38 receives the data from the physiologic transmitter 32 and processes the data to send a trigger signal 42 to the scanner 40 with which it is attached. The raw data 34, filtered data 33 or a trigger signal 42 may be stored in the memory device 43. The receiver 38 may be configured to create a log of the data which may be transmitted at periodic intervals or in response to a transmit command. The processor 41 may also monitor operation of the receiver and identify error states in the receiver 38. The error states may similarly be stored in the memory device 43 and incorporated into the log data.

The physiologic receiver 38 connects to the MRI or CT scanner using a cable 100 configured according to the application requirements. For an MRI scanner, a fiber optic cable may be required, and for a CT scanner, a cable with copper or other metal conductors may be required. Further, scanners from difference manufacturers may require different configurations of cables 100. Each cable 100 may require certain conductors be connected to certain pins of connectors or may, for example, require a set of conductors configured to transmit data via a network protocol, such as Ethernet. The physiologic receiver 38 may be configured to be used for both MRI and CT applications and for different scanners. Ports 104 on the receiver 38 allow for the connection of both MRI and CT scanner connectors 102. According to the illustrated embodiment, the physiologic receiver 38 includes multiple ports 104 where, for example, one port may be used for MRI scans and a second port may be used for CT scans. Optionally, a single port 104 may be included on the physiologic receiver 38 with internal logic circuits configurable to provide the appropriate signals to the port 104 as a function of the cable 100 connected to the port 104. It is also contemplated that the receiver 38 includes one or more ports, such as a Universal Serial Bus (USB) port, configured to communicate with an external device, for example, to transmit log data for remote processing.

The physiologic receiver 38 is able to adjust for connection to an MRI scanner or CT scanner by reading an identification module 101 in the cable 100. The identification module 101 may be incorporated, for example, in the electrical connector 102 for the cable 100. The identification module 101 may be, for example, a set of jumpers corresponding to a bit pattern, an identification resistor having a different value for different lead sets, or any other suitable method of identifying the lead set. The physiologic receiver 38 may be configured to detect the identification module 101 and determine whether the trigger monitoring system 30 is to be used for an MRI scan or a CT scan. Based on the host scanner 40, the physiologic receiver 38 will adjust the type and format of the data that is communicated. The physiologic receiver 38 may be configured to transmit a signal to the physiologic transmitter 32 to indicate whether the cable 100 connected is configured for an MRI scan or a CT scan such that the physiologic transmitter 32 may activate the appropriate position indicator lights 78, 80, as discussed above.

Figure 7:
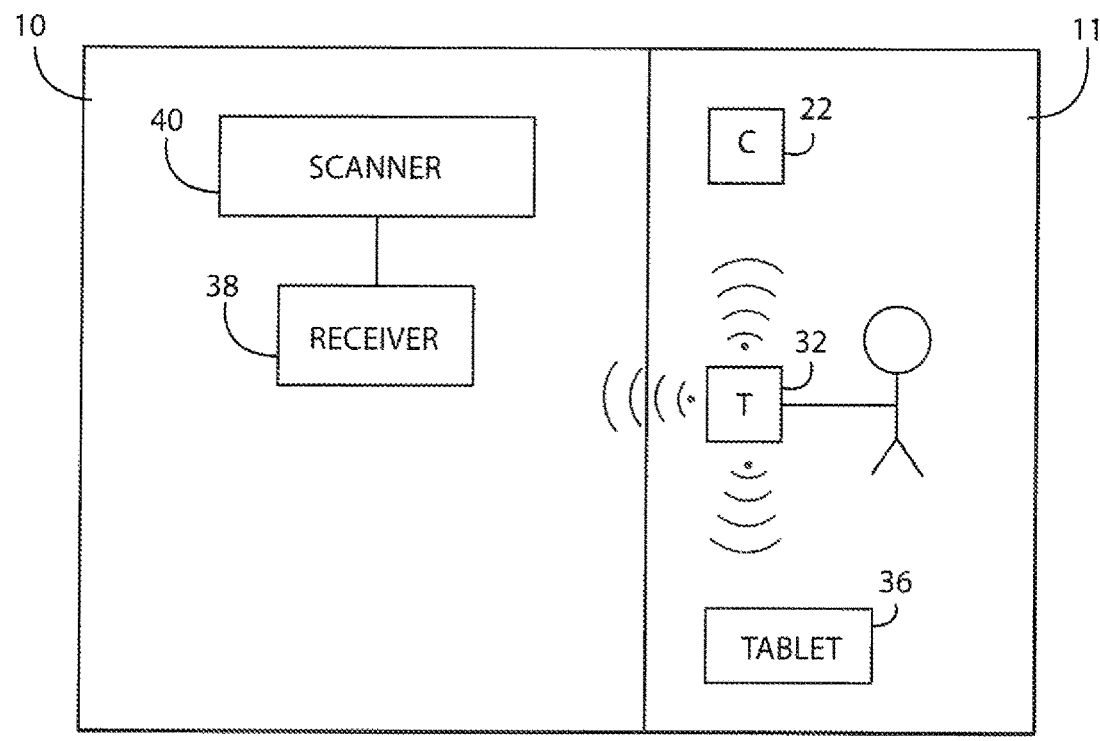
FIG. 7 is an exemplary embodiment of the MRI scan room of FIG. 1, incorporating the trigger monitor system according to one embodiment of the present invention, and showing the patient exterior to the scan room.

Referring next to FIG. 7, in operation, the trigger monitor system 30 provides trigger monitor communication between devices inside the scan room 10 and external to the scan room, such as in control room 11. The wireless functionality of the trigger monitor system 30 facilitates operation both during the scan and outside the scan (e.g., pre-scan or post-scan). During the scan, cable management is simplified by eliminating cables extending between the physiologic sensors and a cabled acquisition module. Additionally, power cables and the potential for interfering emissions from the cables are eliminated by utilizing a rechargeable battery in the system 30. Initial preparation of the patient is also improved by allowing the technician or other medical personnel to arrange the electrodes and leads on the patient outside of the scan room 10. The patient and the physiologic transmitter 32 may then be moved into the scan room 10 for the scan. Improved visualization of the waveform data during scanning is also realized using, e.g., mobile tablet computers 36.

Typically, physiologic sensors must be attached to the patient within the scan room 10. Because of the wireless functionality of the system, the physiologic transmitter 32 may be installed on the patient outside of the scan room 10. In this respect, the operator can make sure that the physiological acquisition equipment is functioning before entering the scan room 10. The physiological acquisition equipment can also be installed on the patient in an examination room, where there is more room and comfort to the patient, as well as reducing the overall time a patient is in the scan room 10, which, in turn, permits increased utilization of the scanners. When it is shown that the physiological acquisition equipment is functioning properly, the patient can be brought into the scan room 10 or control room 11.

The wireless functionality also allows the operator to view the physiologic waveforms sent from the physiologic transmitter 32 on a tablet display 90 or on a computer display 22 from a remote location, such as a location outside of the scan room 10. The tablet display 90 can also be viewed from within the scan room 10 where the operator can easily move around with the tablet 36 and hold it easily in their hands during set up and scanning of the patient.

Figure 8:
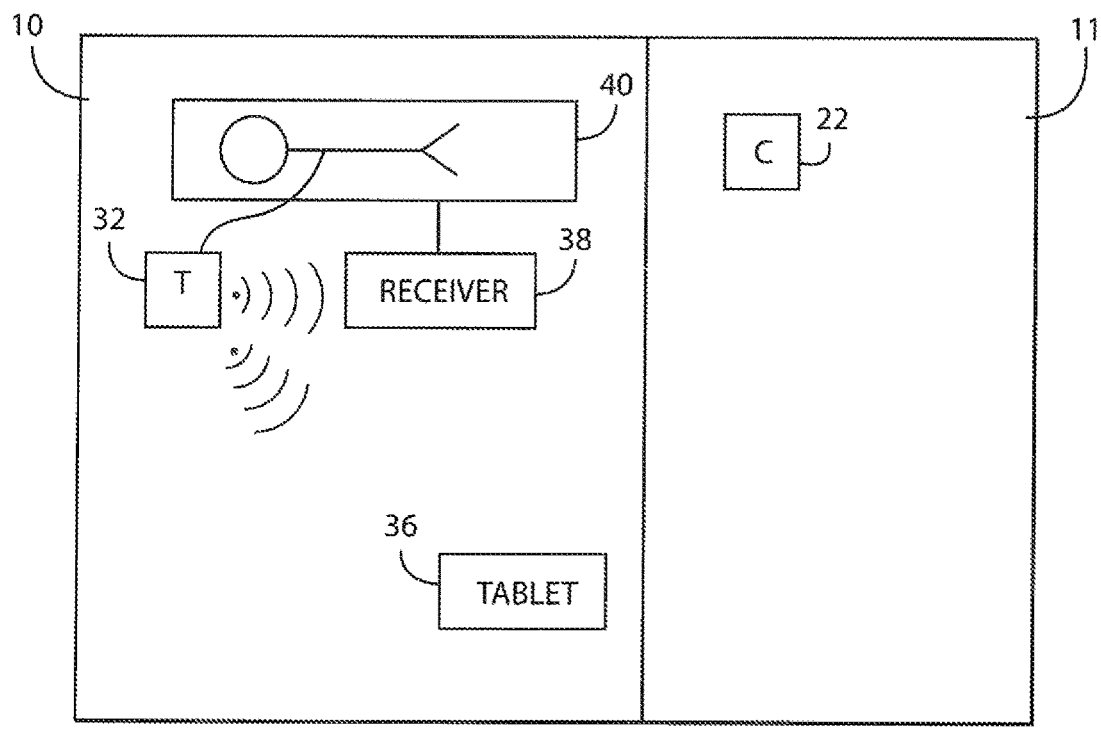
FIG. 8 is an exemplary embodiment of the MRI scan room of FIG. 1, incorporating the trigger monitor system according to one embodiment of the present invention, and showing the patient in the interior of the scan room.

Referring next to FIG. 8, when the patient is being scanned, the physiologic transmitter 32 is conveniently attached to the patient's body while the patient is lying down on the sliding platform 19. While the patient is being scanned, the operator can continue to view the physiologic waveforms from any location inside or outside the scan room 10, from the tablet 36, another computer display 22, or the scanner display 48.

It is contemplated that the trigger monitoring system 30 is conveniently interchangeable between MRI and CT systems. Since many clinical sites run multiple scanners 40, a single physiologic transmitter 32 and receiver 38 may be utilized with both MRI and CT systems. Different leads 56 to the physiologic sensors and different cables 100 to the host scanners 40 may be plugged into each device. According to one embodiment of the invention, the transmitter 32 and receiver 38 are provided as pairs, where the devices are configured to only communicate with the other corresponding unit in the pair. This will avoid the potential for a transmitter 32 in a first scanner for transmitting gating signals that may be received by a receiver 38 in a second scanner. Optionally, a single transmitter 32 can be used in conjunction with multiple physiologic receivers 38, where each receiver 38 may be located by one of the scanners 40 and the transmitter 32 moved as required. Detection by the physiologic transmitter 32 and physiologic receiver 38, respectively, of the MRI or CT connectors ensures that the proper type and format of data is used. An initial setup routine may be executed to establish the transmitter 32 and the desired receiver 38 as a pair to avoid communications between devices on different scanners. Moreover, the physiologic transmitter 32 and physiologic receiver 38, respectively, include the appropriate ports for both MRI and CT system connectors and for different connectors associated with different manufacturers of the scanner 40.

Trigger Monitor System Wireless Technology Protocol

A novel wireless transmission protocol has been developed for use which provides high reliability of transmission between wireless devices with low latency and low jitter. The protocol will be discussed with respect to the aforediscussed trigger monitor system 30. However, it is understood that the protocol may be utilized in various other applications requiring similar reliability with low latency and low jitter. The transmission of waveform data from the physiologic transmitter 32 to the physiologic receiver 38 requires the satisfaction of a number of quality of service requirements that support an overall performance index of the trigger monitor system 30. It is understood that the performance index may be influenced by other factors which are independent of wireless requirements, such as the filtering and gating performed by the processor of the physiologic transmitter prior to data communication.

The quality of services requirements are determined by timing and reliability factors required in the communication of waveform data for image synchronization. For example, the physiologic transmitter 32 sends triggering information to the host scanner 40 based on ECG, PP and RESP waveforms. The waveform with the finest temporal resolution is the ECG waveform, thus driving the desired timing requirements. The timing requirements for CT based applications are less stringent as CT applications can successfully trigger anywhere in the 70-80% period of the R-R wave cycle. Therefore, MRI timing requirements set the standard for timing requirements.

Timing requirements are dependent upon low latency and low jitter in the transmission of the gating trigger. As is understood in the art, latency is the duration of time from when a signal is sampled to when it is transmitted and jitter is the repeatability of the latency between multiple samples. According to one embodiment of the invention, it is desired to have a wireless latency less than 10 ms so as to not degrade the diagnostic quality of the exam. Moreover, it is desired to have a wireless jitter less than 2 ms. Jittter that is greater than 2 ms will create heartbeat to heartbeat variation in the collected data thereby reducing the diagnostic quality of the exam.

The trigger monitoring system 30 also relies upon the reliable transmission of the trigger pulse from the physiologic transmitter to the physiologic receiver. False positives (generating a trigger signal other than the desired point of the QRS waveform) will result in an image being acquired when not expected. False negatives (not generating a trigger signal at the desired point of the QRS waveform) will result in a scan not being acquired when expected. Receipt of a false positive trigger may occur, for example, if noise is introduced in the wireless data during transmission. A false negative may occur due, for example, to transmission failures of packets communicated between the transmitter and the receiver.

In MRI and CT imaging, a false negative results in missing images during a scan. Because consecutive scans of a targeted anatomy may be compiled to generate a three-dimensional image of the targeted anatomy, missing scans may result in missing sections of the targeted anatomy and lower quality images. In MRI applications, patients typically remain in place and a missed image can be re-acquired in a subsequent scan with little or no risk to the patient. However, because CT scans utilize x-ray radiation, the impact of missed triggers in CT is greater than in MRI. Missed sections of the targeted anatomy or low quality images may result in a repeated exam that can expose the patient to additional ionizing radiation which may be harmful to the patient. A false positive results in an image being taken at an unexpected or undesired location within a respiratory or cardiac cycle. The extra image may result in motion artifacts being generated within the image, reducing the quality of the image. Thus, it is desirable to minimize false negative and false positive detections during MRI and CT scans.

Figure 9:
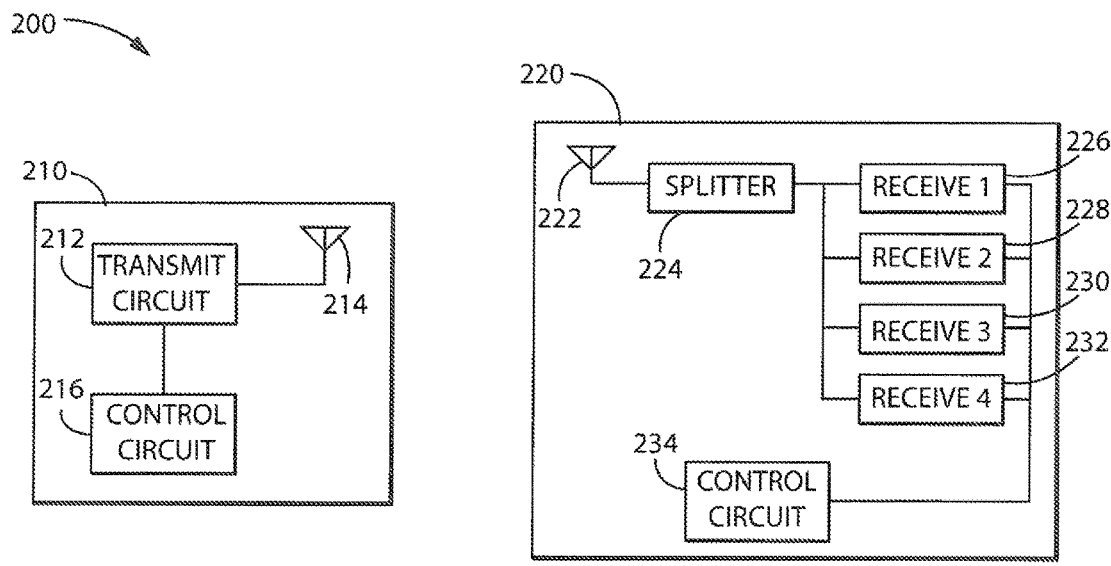
FIG. 9 is a block diagram representation of a wireless communication system providing communications between a transmitter and a receiver according to one embodiment of the present invention.
Figure 10:
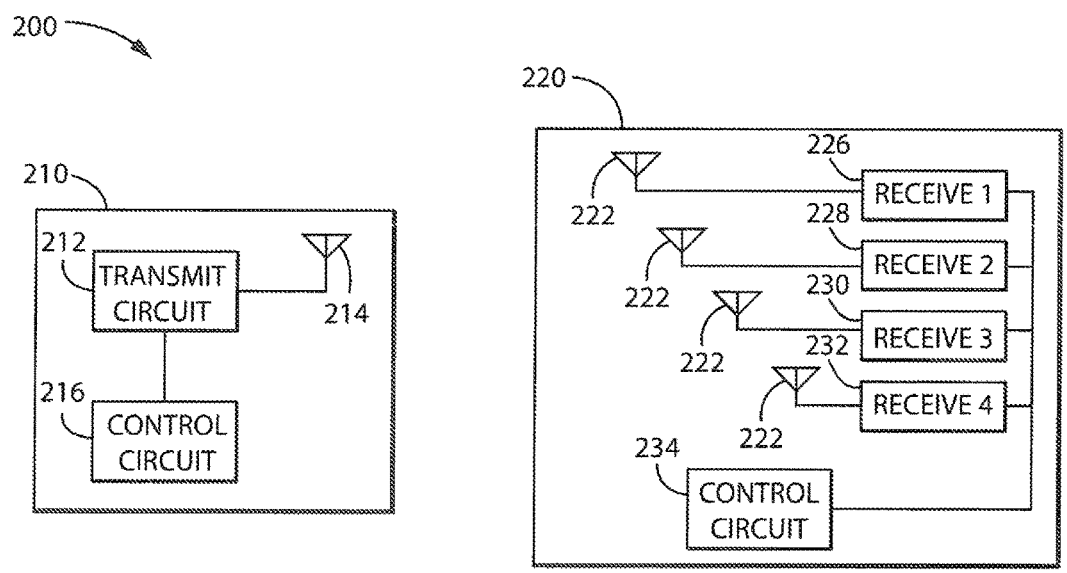
FIG. 10 is a block diagram representation of a wireless communication system providing communications between a transmitter and a receiver according to another embodiment of the present invention.

Referring now to FIGS. 9 and 10, a wireless transmission system 200 providing improved reliability and implementing the proprietary wireless protocol is shown. The wireless transmission system 200 will be discussed with respect to the trigger monitoring system 30 described herein. However, it is understood that the protocol and transmission system 200 may be implemented for other applications requiring highly reliable transmissions without deviating from the scope of the invention. In the illustrated embodiment of the present invention, a transmitter 210 includes a transmit circuit 212, an antenna 214, and a control circuit 216. The control circuit receives data from external sources, such as the physiologic sensors, and processes the data for transmission. It is contemplated that the control circuit may include a processor executing a series of instructions stored in memory, digital or analog integrated circuits configured to perform specific functions, or a combination thereof. The processed data is sent from the control circuit 216 to the transmit circuit 212 where it is converted into a suitable signal, such as a radio frequency (RF) signal for transmission by the antenna 214.

As illustrated in FIG. 9, the receiver 220 includes an antenna 222, a splitter 224, multiple receive circuits 226, 228, 230, 232 and a control circuit 234. It is contemplated that the control circuit may include a processor executing a series of instructions stored in memory, digital or analog integrated circuits configured to perform specific functions, or a combination thereof. The antenna 222 receives the RF signal from the transmitter 210 and sends it to the splitter 224. The splitter 224 may identify and separate multiple signals received at the antenna 222 and using, for example, frequency demodulation, amplitude demodulation, de-multiplexing, time-division, or any other suitable method of splitting the multiple signals complementary to the method of combining or transmitting the multiple signals utilized by the transmitter 210. The splitter 224 may send the separated RF signals to each of the receive circuits 226, 228, 230, 232 or, optionally, the splitter 224 may route the separated RF signals to one of the receive circuits 226, 228, 230, 232 based, for example, on the frequency of the RF signal from the transmitter 210. Each receive circuit 226, 228, 230, 232 converts the RF signal to a digital or analog signal suitable for processing by the control circuit 234. The control circuit 234 extracts the data from the signals and may perform additional processing of the data or transmit the data to another device, for example, via a wired network connection or, for the physiologic receiver 38, via the cable 100 to the host scanner 40. According to the embodiment illustrated in FIG. 9, the receiver 220 includes a single antenna 222 and a splitter 224 to send the RF signals to each receive circuit 226, 228, 230, 232. As illustrated in FIG. 10, multiple antennas 222 may be provided with one antenna 222 in communication with each receive circuit 226, 228, 230, 232. According to still another option, multiple antennas 222 may be routed through the splitter 224 and/or to each of the receive circuits directly 226, 228, 230, 232. Each receive circuit 226, 228, 230, 232 is tuned to a preselected frequency. Optionally the frequency of each receive circuit 226, 228, 230, 232 may be configurable, however, during operation, it is preferred that each receive circuit remain at a single frequency. In the illustrated embodiment, four receive circuits 226, 228, 230, 232 are illustrated. It is contemplated that the transmission protocol described herein may be practiced with various other numbers of receive circuits 226, 228, 230, 232, the number selected according to application requirements without deviating from the scope of the invention. Four receive circuits 226, 228, 230, 232 provides a desired quality of service for the trigger monitor system 30 described herein.

The transmitter 210 sends data to the receiver 220 at multiple frequencies to increase reliability of the transmission. The delivery of data is made more reliable as a result of the frequency diversity because delivery at the at least four different frequencies results in back-up delivery in the case of interference at a particular channel frequency. During operation, each receive circuit 226, 228, 230, 232 remains at a specific channel, or frequency, and each receive circuit 226, 228, 230, 232 is preferably set to a different wireless channel. For each data sample sent to the receiver 220, the transmitter 210 is configured to transmit at varying frequencies and transmits the same data packet at the frequency corresponding to the channels at which each of the different receiver circuits 226, 228, 230, 232 are set. Use of multiple frequencies improves the probability that one of the channels will be clear to successfully transmit the data packet.

Figure 11:
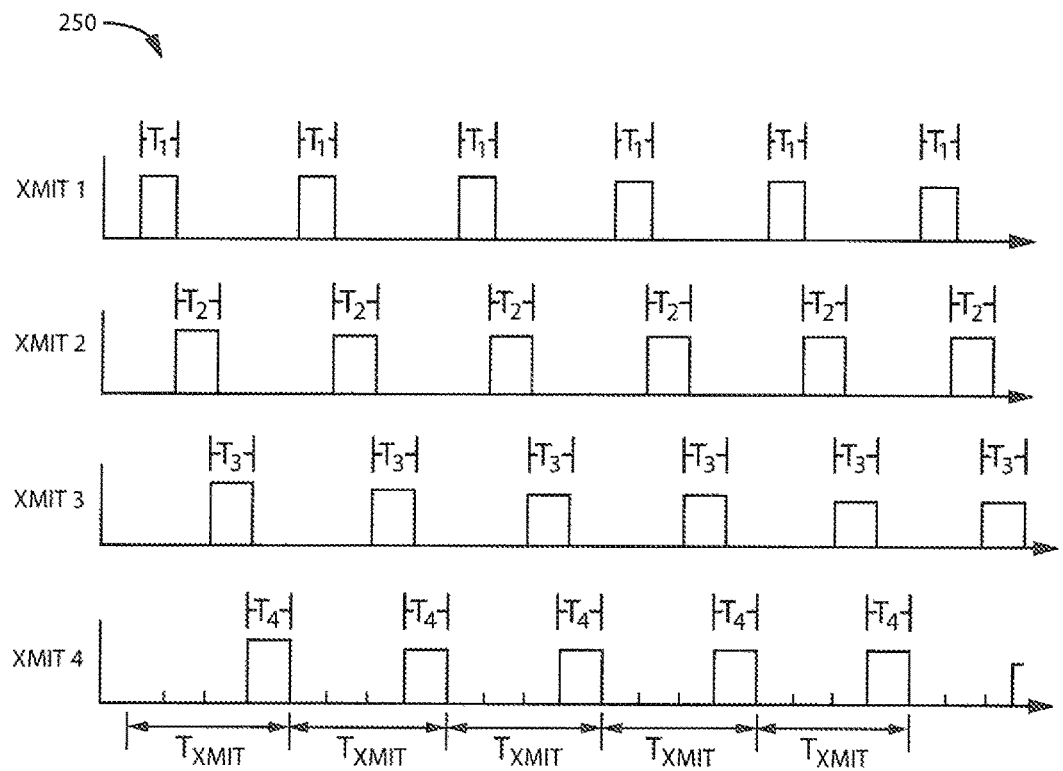
FIG. 11 is a graphical representation of an exemplary transmission schedule for the communication system.

The transmitter 210 sends data to the receiver 220 at multiple frequencies according to a transmission schedule 250 as illustrated, for example, in FIG. 11. According to the illustrated embodiment, the transmitter is scheduled to transmit data at four different frequencies. Transmission occurs at a periodic interval, having a duration, $T_{XMIT}$, which may be predefined or configurable. For the trigger monitor system 30, it is desirable to have a low latency, therefore, the duration, $T_{XMIT}$, is preferably less than 5 ms and, more preferably is about 1 ms. Within each periodic interval, the transmitter 210 sends the data at each of the frequencies of the receiver circuits 226, 228, 230, 232. A first transmission XMIT1 occurs at a first frequency during a first portion, $T_1$, of the duration, $T_{XMIT}$, of the periodic cycle. A second transmission XMIT2 occurs at a second frequency during a second portion, $T_2$, of the duration, $T_{XMIT}$, of the periodic cycle. A third transmission XMIT3 occurs at a third frequency during a third portion, $T_3$, of the duration, $T_{XMIT}$, of the periodic cycle. A fourth transmission XMIT4 occurs at a fourth frequency during a fourth portion, $T_4$, of the duration, $T_{XMIT}$, of the periodic cycle. The transmitter 210 achieves frequency diversity, therefore, by sending four transmissions XMIT1-XMIT4 of the same data packet at four frequencies during each transmission period.

At the end of each transmission interval, the receiver 220 may verify that the data was transmitted successfully. According to one embodiment, the receiver 220 extracts the data sent from each data packet at each of the four frequencies. The data may be stored in memory on the receiver 220. Because the same data was used to generate the data packet which was transmitted at each frequency, the extracted data should be the same. The control circuit 234 in the receiver may compare the data extracted from each frequency against each other. If the data from each of the data packets is identical, the receiver confirms that the data was transmitted successfully. Optionally, if at least three frequencies are used to transmit the data, the control circuit 234 may use a majority voting method, where if the data from over half of the data packets is identical, the control circuit 234 uses the data from the majority of the data packets that are identical and confirms that the data was transmitted successfully. If the data from at least half of the data packets are different from each other, the control circuit 234 indicates that the data was not transmitted successfully and may ignore the data from that transmission interval.

According to another embodiment, the transmitter 210 may generate a checksum based on the data included in the data packet. The receiver 220 extracts the data and the checksum sent in each data packet at each of the four frequencies. The receiver 220 determines a checksum based on the data extracted from the data packet and compares the calculated checksum to the transmitted checksum. If receiver 220 determines that a data packet from any of the four frequencies was successfully transmitted as a result of matching checksums, the receiver 220 may utilize the data from that data packet and confirms that the data was transmitted successfully. It the receiver 220 determines that the calculated checksum does not match the transmitted checksum at any of the frequencies, the receiver 220 indicates the data was not transmitted successfully and may ignore the data from that transmission interval.

Spatial diversity may be achieved by using multiple receiving antennas. The receiving antennas are spatially displaced and act independently. Optionally, a circular antenna or antenna array may be configured to receive the transmissions from multiple polarizations. Multipath propogation can, for example, adversely affect the quality of service on a given antenna/radio pair, but the multipath impact will be different on the other antenna/radio pairs. Use of multiple antennas reduces the probability that multipath effects will impact overall quality of service. Thus, it is further contemplated that the receiver 220 may include four antennas 222. Each antenna 222 may be in communication with one of the receive circuits 226, 228, 230, 232 and may be configured to receive a transmission at the frequency corresponding to the respective receive circuit 226, 228, 230, 232. Thus, if interference exists along one transmission path, another transmission path may receive the transmission between the transmitter 210 and the receiver.

At the end of each transmission interval, the receiver 220 may execute a verification of successful transmission for the multiple antennas in a manner similar to that described above for transmission at multiple frequencies. The receiver 220 may verify successful transmission based on comparison of the data received at each antenna or, if available, may evaluate a checksum transmitted with the data.

It is further contemplated that the transmitter may employee frequency diversity and spatial diversity together. In other words, data may be transmitted at multiple frequencies and received by spatially displaced antennas. Verification of transmitted data may be a two-step process. For example, verification may first determine whether data received from the multiple antennas was successful. If the receiver 220 successfully received data at a majority of antennas, the receiver 220 may next determine whether the received data is the same across a majority of the frequencies. If the data is the same at the majority of antennas and across a majority of the transmission frequencies, the transmission was successful. In the event a checksum is utilized, any data packet successfully received, as verified by the checksum, indicates successful transmission.

Figure 12:
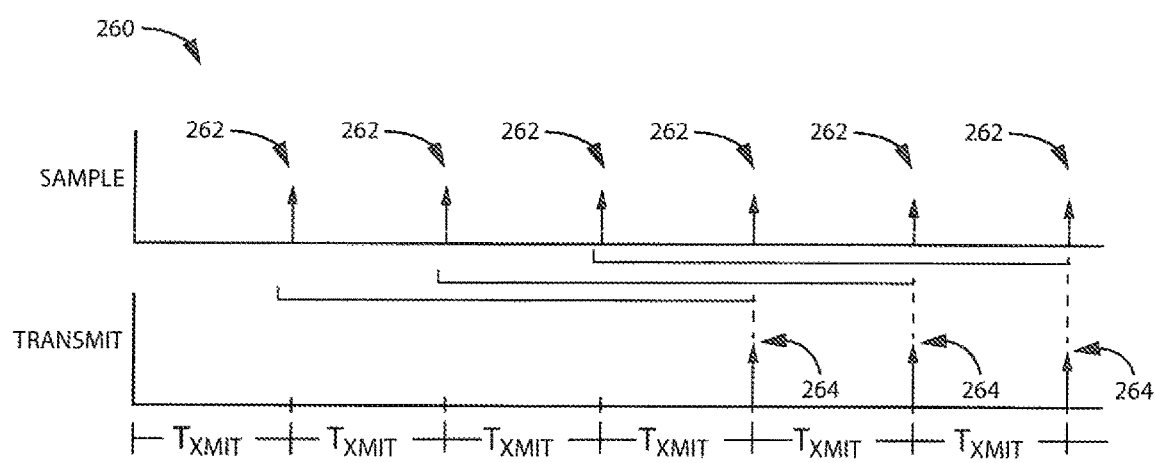
FIG. 12 is a graphical representation of exemplary data sampling and transmission for the communication system.

As yet another method of ensuring reliable data transmission, the control circuit 216 of the transmitter 210 uses time diversity in which multiple samples of a signal are obtained prior to transmitting the signal to the receiver 220. With reference to FIG. 12, according to the illustrated embodiment, four samples 262 of a signal are taken prior to transmission of the signal. As illustrated, the transmitter obtains four samples 262; however, it is contemplated that various other numbers of samples may be utilized without deviating from the scope of the invention. The control circuit 216 of the transmitter 210 stores the value of each sample in memory on the transmitter 210. Preferably, a first-in-first-out (FIFO) buffer is established having a length equal to the number of samples to be transmitted. At each transmission interval, the transmitter 210 obtains the present value of the data to be transmitted and stores it in the most recent location in the FIFO buffer, shifting the remaining values down one location. The transmitter 210 then includes each of the values in the FIFO buffer in the data packet. According to the illustrated embodiment, initial loading of the FIFO buffer may occur, for example, by not making a transmission 264 at the first three sample instances 262. With the fourth sample 262, a transmission 264 begins to occur between the transmitter 210 and the receiver 220. Optionally, other preloading techniques may occur, for example, sending a single sample 262 in a transmission 264 with the first sample, sending two samples 262 in a transmission 264 with the second sample 262, sending three samples 262 in a transmission 264 with the third sample 262, and sending four samples 262 in subsequent transmissions 264. At each transmission 264 the four previous samples 262 are transmitted. If the duration, $T_{XMIT}$, of the sample period is one millisecond, then a four millisecond latency exists from obtaining the first sample to transmitting the data to the receiver 220. However, if one of the transmissions 264 is not successful, the data is inherently retransmitted during the next transmission 264. Each sample 262 is retransmitted four times. The control circuit 234 of the receiver 220 may read the sample 262 from each transmission 264 and, for example, execute according to a majority of the values for one sample 262 being the same. If, for example, any three of the values for a sample 262 are the same, the control circuit 234 discards the conflicting value as an erroneous transmission 264 and executes based on the three common values. Although the illustrated embodiment obtains four samples 262 per transmission 264, it is contemplated that at least two, or various other numbers of, samples 262 may be sent during each transmission 264 without deviating from the scope of the invention. According to still another aspect of the invention, different numbers of samples may be obtained for data corresponding to different physiologic parameters. For example, four samples 262 may be obtained for cardiac data while eight samples may be obtained for trigger data.

Although the control circuit 234 of the receiver 220 may execute according to a majority of values of a sample 262 being the same, it is also contemplated that the data may include, for example, a checksum or other means of error detection. If the control circuit 234 determines based on the checksum that a received message is correct, it identifies the packet as containing good data. The data may then be stored and relied upon for future execution. Thus, if the transmitter 210 is using a four sample redundancy but three packets in a row are lost, the final packet will still contain valid data and the receiver 220 may rely on the single received sample 262 for execution.

It is further contemplated that the transmission protocol may utilize all three of the afore-described diversity techniques, namely frequency diversity, spatial diversity, and time diversity. Verification may be a multiple step process, verifying that one of the diversity techniques is successful prior to verifying that a subsequent diversity technique is successful. With multiple diversity techniques, it may be preferable to include a checksum, such that verification of successful transmission of any one data packet based on the checksum, results in the data from that data packet being used by the receiver 220.

It is also contemplated that multiple transmitters 210 and receivers 220 may be operating within range of each other. To avoid reception of and processing of data packets from other transmitters 210 and/or receivers 220, each transmitter 210 and receiver 220 may be established as a pair. The transmitter 210 and receiver 220 may be configured initially, for example, via hardware and/or software switches to only communicate with a paired device. Optionally, each transmitter 210 and receiver 220 may be configurable to communicate with multiple other devices; however, an initialization routine may be executed to connect the transmitter 210 and receiver 220 as a pair based, for example, on addresses or other identification within each device. During operation, although both the transmitter 210 and the receiver 220 may be configured to transmit a message to the other device, each transmission is unidirectional, requiring no acknowledgement. Thus, the source and/or destination address or other identifier is included in the data packet. The receiving device verifies that it is either the intended recipient or receiving a transmission from its corresponding paired device. If the received transmission is either not intended for the receiving device or not sent from its corresponding device, the data packet is discarded.

Thus, the wireless protocol disclosed herein utilizes multiple methods of improving reliability of data transmission between two devices without requiring an acknowledge signal. The data may be transmitted at multiple frequencies to avoid interference at any one frequency. The data may be transmitted and/or received utilizing multiple antennas or multi-directional antennas to avoid interference along any one transmission path. The data may also be saved and transmitted in batches such that each data sample is transmitted multiple times to avoid the loss of any one data transmission. It is contemplated that various combinations of the afore-mentioned techniques may be utilized to achieve improved reliability of transmissions. It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

We claim:

1. A wireless communication system, comprising:
   a transmitter including:
      a control circuit configured to prepare a data packet for transmission at a periodic interval,
      a transmit circuit in communication with the control circuit and configured to convert the data packet to a plurality of radio frequency (RF) signals for transmission, wherein each RF signal includes the data packet and each RF signal has a different frequency, and
      an antenna in communication with the transmit circuit and configured to transmit the RF signal, wherein the transmit circuit transmits each RF signal within the periodic interval; and
   a receiver including:
      at least one antenna configured to receive the RF signal;
      at least one receive circuit, each receive circuit in communication with the at least one antenna and configured to convert the RF signal to a data packet, and
      a control circuit in communication with each receive circuit and configured to extract data from the data packet, wherein:
      the receiver receives the RF signals at each of the frequencies, converts each RF signal back to the data packet, and verifies that the data packet was transmitted successfully.

2. The wireless communication system of claim 1 wherein the receiver includes an antenna and a receive circuit tuned to each of the frequencies at which the RF signals are transmitted and the antenna and the receive circuit are configured to receive the RF signal at the corresponding frequency.

3. The wireless communication system of claim 1 wherein:
   the receiver includes one antenna;
   the receiver includes a plurality of receive circuits, each receive circuit tuned for one of the frequencies at which the transmitter transmits RF signals;
   the wireless communication system further includes a splitter in communication with the antenna and each receive circuit;
   the splitter identifies the frequency of each RF signal received by the antenna; and
   the splitter routes the RF signal to the corresponding receive circuit tuned for the frequency of the RF signal.

4. The wireless communication system of claim 1 wherein the receiver verifies that the data packet was transmitted successfully by comparing the data packets received at each of the frequencies and when a majority of the data packets are the same, the receiver uses one of the majority of identical data packets.

5. The wireless communication system of claim 1 wherein:
   the transmitter includes a checksum in the data packet; and
   the receiver verifies that the data packet was transmitted successfully by determining that the checksum received corresponds to the data present in the data packet for at least one of the frequencies at which the data packet was transmitted.

6. The wireless communication system of claim 1, wherein:
   the transmitter further includes memory configured to store a plurality of values of data to be included in the data packet on a first-in-first-out basis; and
   the control circuit of the transmitter includes the plurality of values in the data packet.

7. The wireless communication system of claim 6 wherein:
   the control circuit of the receiver extracts the plurality of values from the data packet received at each frequency;
   the receiver further includes memory configured to store the plurality of values extracted from each of the data packets;
   the control circuit in the receiver compares each value for a transmitted signal extracted from the data packet at one frequency to the corresponding value from each of the data packets at the other frequencies at which it is transmitted; and
   the control circuit verifies that each value was transmitted successfully when a majority of the corresponding values from the data packet, received at each of the frequencies, is the same.

8. The wireless communication system of claim 6 wherein:
   the control circuit of the transmitter includes a checksum in the data packet;
   the control circuit of the receiver verifies that the checksum in the data packet corresponds to the plurality of values in the data packet; and
   the control circuit in the receiver verifies that each value was transmitted successfully when the checksum for at least one of the data packets in which each value is transmitted corresponds to the plurality of values in the data packet.

9. The wireless communication system of claim 6, wherein:
   the receiver includes a plurality of antennas;

each antenna is spatially displaced from the other antennas; and each antenna is in communication with one of the receive circuits.

10. The wireless communication system of claim 7, wherein latency in transmission of the data packet is less than ten milliseconds.

11. The wireless communication system of claim 8, wherein jitter between repeated transmission of the data packet is less than two milliseconds.

12. A method of wireless communication, the method comprising the steps of:

receiving a data signal at a control circuit in a transmitter;

generating a data packet which includes at least one value of the data signal in the control circuit;

converting the data packet to a plurality of RF signals, wherein each RF signal includes the data packet and each RF signal has a different frequency;

transmitting each of the RF signals within a periodic interval;

receiving each of the RF signals at a receiver in communication with the transmitter;

extracting the data packet from each of the RF signals in a control circuit in the receiver; and evaluating the data packets to verify that the data packet was transmitted successfully.

13. The method of wireless communication of claim 12 wherein the step of evaluating the data packets to verify that the data packet was transmitted successfully further comprises:

comparing the data packets extracted from each of the RF signals to each other; and determining the data packet was transmitted successfully when a majority of the data packets are identical.

14. The method of wireless communication of claim 12 wherein the control circuit of the transmitter generates a checksum for the data packet and transmits the checksum along with the data packet and wherein the step of evaluating the data packets to verify that the data packet was transmitted successfully further comprises:

determining a checksum for each data packet in the control circuit of the receiver; and determining the data packet was transmitted successfully when the checksum determined on the receiver matches the checksum transmitted from the transmitter.

15. The method of wireless communication of claim 12 further comprising the steps of:

storing a plurality of values of the data signal in a memory device in the transmitter on a first-in-first-out basis;

including each of the plurality of values in the data packet when the data packet is generated;

extracting each of the plurality of values from the data packet received at each different frequency by the receiver; and storing the plurality of values extracted from the data packets received at each different frequency in a memory device in the receiver.

16. The method of wireless communication of claim 15 wherein the step of evaluating the data packets to verify that the data packet was transmitted successfully further comprises:

comparing the value of the data signal extracted from the data packet at one frequency to the corresponding value of the data signal extracted from each of the other data packets transmitted at different frequencies; and determining that each value of the data signal was transmitted successfully when a majority of the corresponding values of the data signal from the data packets, received at different frequencies, is identical.

17. The method of wireless communication of claim 15 wherein the control circuit of the transmitter generates a checksum for the data packet and transmits the checksum along with the data packet and wherein the step of evaluating the data packets to verify that the data packet was transmitted successfully further comprises:

determining a checksum for each data packet in the control circuit of the receiver; and determining that each value of the data signal in one of the data packets was transmitted successfully when the checksum determined on the receiver matches the checksum transmitted from the transmitter.

18. The method of wireless communication of claim 12 wherein the receiver includes a plurality of antennas, each antenna is spatially displaced from the other antenna, and wherein the step of receiving each of the RF signals at a receiver in communication with the transmitter further includes:

receiving each of the RF signals at each antenna;

transmitting each of the RF signals from each antenna to a receive circuit in communication with the antenna; and extracting the data packet from each of the RF signals received at each antenna.

19. The method of claim 18 wherein the step of evaluating the data packets to verify that the data packet was transmitted successfully further comprises:

comparing each of the data packets transmitted at one of the frequencies and received at each of the antennas to each other;

determining the data packet at one of the frequencies was transmitted successfully when a majority of the corresponding packets received at each antenna are identical;

comparing the successfully transmitted data packet at each frequency to the successfully transmitted data packet at each of the other frequencies; and determining that the data packet was successfully transmitted when a majority of the successfully transmitted data packets at each frequency are identical.

20. The method of claim 12 wherein the data signal received is from a sensor generating a signal corresponding to a physiological parameter of a patient to which the sensor is connected and wherein the transmitter and receiver are utilized with a medical imaging scanner, the method further comprising the steps of:

processing the data signal in the control circuit of the transmitter to generate at least one of a filtered data signal and a trigger signal;

generating the data packet to include the trigger signal;

extracting the trigger signal from the data packet with the control circuit of the receiver; and transmitting the trigger signal to the medical imaging scanner to initiate acquisition of an image of the patient.

* * * * *